United States Patent [19]

Hofmann et al.

[11] Patent Number: 4,732,895

[45] Date of Patent: Mar. 22, 1988

[54] α-[5-METHYL-2-(PYRIDINYL)-1H-IMIDAZOL-4-YL]SUBSTITUTED-1-PIPERAZINEETHANOLS USEFUL FOR TREATING HYPERTENSION

[75] Inventors: Corris M. Hofmann, Hohokus, N.J.; Howard Newman, Monsey, N.Y.; Andrew S. Tomcufcik, Old Tappan, N.J.

[73] Assignee: American Cyanamid Company, Stamford, Conn.

[21] Appl. No.: 858,633

[22] Filed: May 2, 1986

[51] Int. Cl.$^4$ .................. A61K 31/33; A61K 31/495; C07D 498/00; C07D 403/14

[52] U.S. Cl. .................................... 514/211; 514/252; 540/547; 544/295; 544/364

[58] Field of Search ................ 544/295, 364; 540/547; 514/211, 252

[56] References Cited

U.S. PATENT DOCUMENTS 3,941,789  3/1976  Renth et al. ........................ 544/364
4,440,774  4/1984  Baldwin .............................. 544/364

Primary Examiner—Donald G. Daus
Assistant Examiner—Cecilia Shen
Attorney, Agent, or Firm—Edward A. Conroy, Jr.

[57] ABSTRACT

This disclosure describes novel substituted α-[5-methyl-2-pyridyl-1H-imidazol-4-yl]-1-piperazineethanols which possess hypotensive activity.

23 Claims, No Drawings

α-[5-METHYL-2-(PYRIDINYL)-1H-IMIDAZOL-4-YL]SUBSTITUTED-1-PIPERAZINEETHANOLS USEFUL FOR TREATING HYPERTENSION

BRIEF SUMMARY OF THE INVENTION

This invention is concerned with new compounds having hypotensive activity of the general formula I:

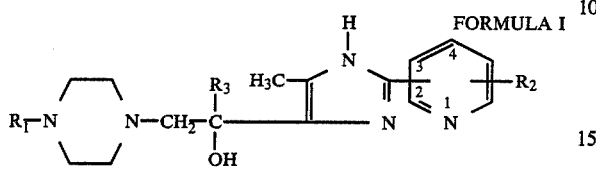

FORMULA I wherein $R_1$ is selected from the group consisting of phenyl, substituted phenyl [wherein the substituents are selected from the group consisting of halogen, trifluoromethyl, alkyl($C_1$–$C_3$) and alkoxy($C_1$–$C_3$)] thiazolyl, pyrimidinyl and 2-chlorodibenzo[b,f][1,4]oxazepin-11-yl; $R_2$ is selected from the group consisting of hydrogen and alkyl($C_1$–$C_3$); $R_3$ is selected from the group consisting of hydrogen, alkyl($C_1$–$C_3$) and phenyl; the bond to the pyridine ring may be at the 2, 3 or 4 position and the pharmacologically acceptable acid addition salts thereof.

In addition this invention is concerned with the group of intermediates used to prepare the active compounds of Formulas I which are represented by the following general formula II:

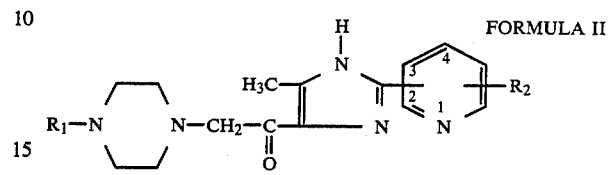

FORMULA II wherein $R_1$ and $R_2$ are as described above for formula I.

DETAILED DESCRIPTION OF THE INVENTION

The compounds of Formula I, wherein $R_3$ is hydrogen, may be prepared as outlined below:

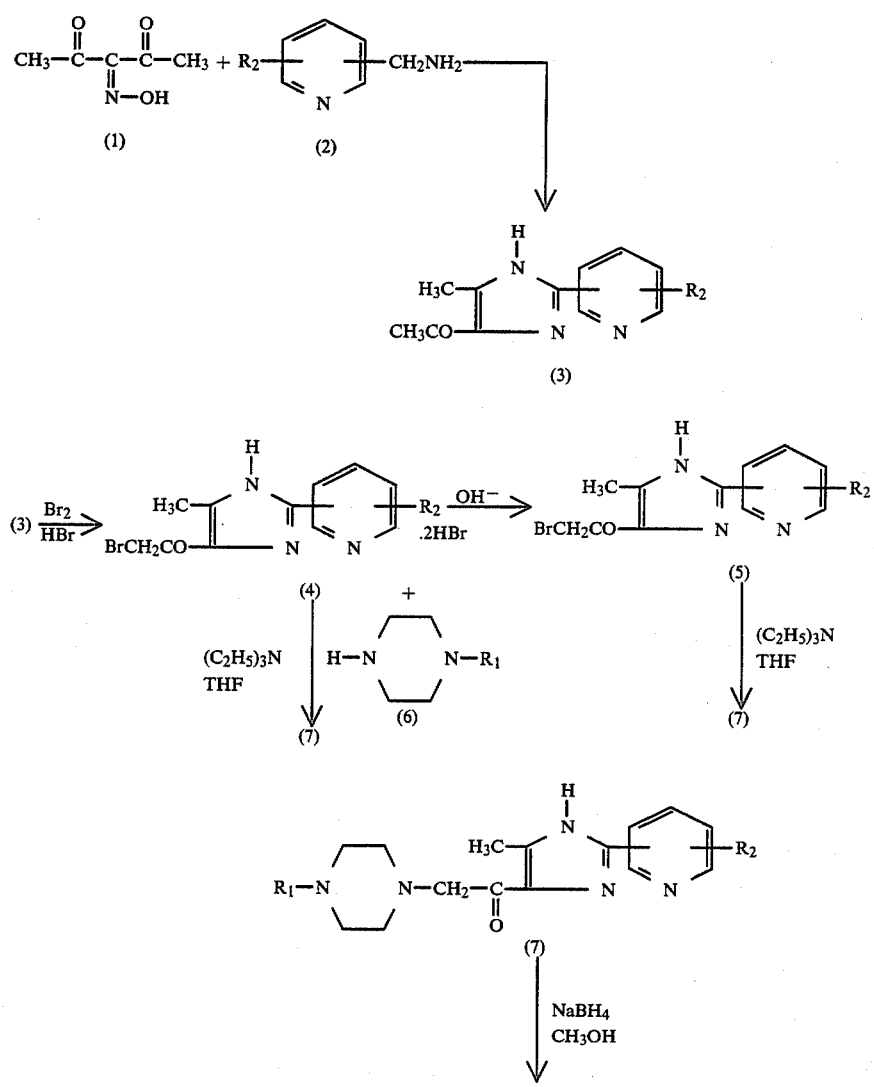

-continued

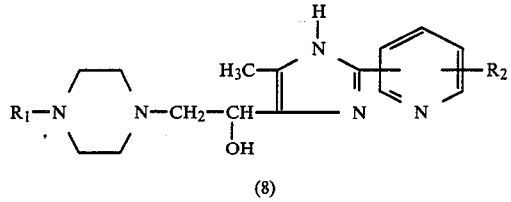

(8)

In accordance with the above scheme 2,3,4-pentanetrione, 3-oxime (1) is reacted with a pyridylmethylamine (where $R_2$ is as described above) in acetonitrile at reflux and then chilled, giving a 1-[5-methyl-2-(substituted pyridyl)-1H-imidazol-4-yl]ethanone (3). The ethanone (3) is then reacted with bromine in hydrobromic acid at 70°–90° C. giving a 2-bromo-1-[5-methyl-2-(substituted pyridyl)-1H-imidazol-4-yl]ethanone dihydrobromide (4) which may be converted to the base (5) by treatment with an aqueous base. Either the dihydrobromide (4) or base (5) in dry tetrahydrofuran is then reacted with a substituted piperazine (6) (where $R_1$ is as described above) and triethylamine giving an intermediate 1-[5-methyl-2-(substituted pyridyl)-1H-imidazol-4-yl]-2-(4-substituted-1-piperazinyl)ethanone (7) which is converted to a final product (8) by treatment with sodium borohydride in methanol with cooling followed by adjustment to pH 7–8 with glacial acetic acid and extraction into an organic solvent.

The compounds of Formula I, wherein $R_3$ is alkyl(-$C_1$–$C_3$) or phenyl, may be prepared as outlined below:

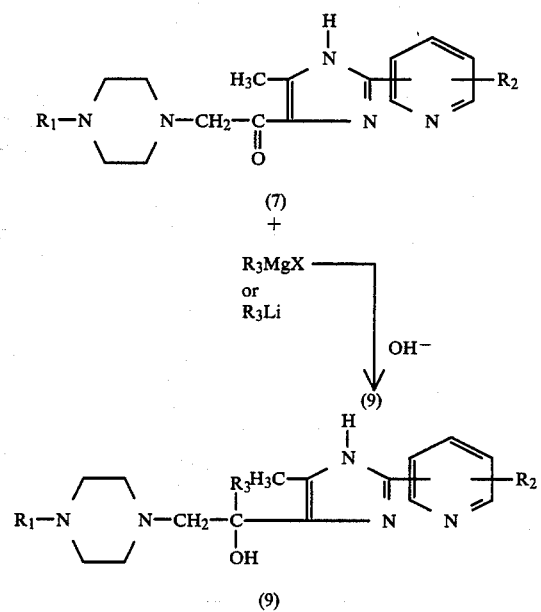

In accordance with the above scheme, a 1-[5-methyl-2-(substituted pyridyl)-1H-imidazol-4-yl]-2-(4-substituted-1-piperazinyl)ethanone (7), where $R_1$ and $R_2$ are as described above, is treated with a Grignard or lithium reagent, where $R_3$ is alkyl($C_1$–$C_3$) or phenyl and X is chlorine, bromine or iodine, in a suitable solvent such as diethyl ether, tetrahydrofuran, 1,2-dimethoxyethane and the like. The resultant adduct is then treated with dilute alkali giving the desired final product of structure (9).

The novel compounds of the present invention are physiologically active and therefore, useful in the pharmaceutical field. In particular, these compounds possess anti-hypertensive activity at non-toxic doses and, as such, are useful as hypotensive agents. The hypotensive properties of the compounds of the present invention have been shown when orally administered to mammals, specifically warm-blooded animals as described below.

The novel compounds of the present invention were tested for anti-hypertensive activity in a procedure using spontaneously hypertensive rats (SHR) (average mean arterial blood pressure 160 mmHg) as follows: One male adult SHR (16–20 weeks old) weighing about 300 grams (Taconic Farms, Germantown, N.Y.) is dosed by gavage with the test compound at 100 mg/kg with 0.9% sodium chloride loading at 25 mg/kg at zero hour. A second identical dose is given at 24 hours without saline loading and the mean arterial blood pressure (MABP) of the conscious rat is measured directly by femoral artery puncture at 28 hours. A second or third SH rat may be needed depending on the results of the first rat [Chan, et al., Pharmacologist, 17, 253 (1975)].

The results of this test on representative compounds of this invention appear in Table I.

TABLE I

| Hypotensive Activity in Spontaneously Hypertensive Rats | |
|---|---|
| Compound | Average MABP mm Hg (No. of Rats) |
| α-[5-methyl-2-(3-pyridinyl)-1H—imidazol-4-yl]-4-phenyl-1-piperazineethanol | 88(2) |
| 4-(4-fluorophenyl)-α-[5-methyl-2-(3-pyridinyl)-1H—imidazol-4-yl]-1-piperazineethanol | 90(2) |
| α-[5-methyl-2-(3-pyridinyl)-1H—imidazol-4-yl]-4-[3-(trifluoromethyl)phenyl]-1-piperazineethanol | 115(3) |
| 4-(2-methoxyphenyl)-α-[5-methyl-2-(3-pyridinyl)-1H—imidazol-4-yl]-1-piperazineethanol | 102(2) |
| 4-(4-fluorophenyl)-α-methyl-α-[5-methyl-2-(3-pyridinyl)-1H—imidazol-4-yl]-1-piperazineethanol | 95(2) |
| 4-(4-chlorophenyl)-α-[5-methyl-2-(3-pyridinyl)-1H—imidazol-4-yl]-1-piperazineethanol | 115(2) |
| 4-(4-methoxyphenyl)-α-[5-methyl-2-(3-pyridinyl)-1H—imidazol-4-yl]-1-piperazineethanol | 124(3) |
| 4-(4-fluorophenyl)-α-[5-methyl-2-(3-pyridinyl)-1H—imidazol-4-yl]-1-piperazineethanol, tartarate | 98(2) |
| 4-(2-chlorodibenzo[b,f][1,4]oxazepin-11-yl)-α-[5-methyl-2-(3-pyridinyl)-1H—imidazol-4-yl]-1-piperazineethanol | 120(3) |
| α-[5-methyl-2-(3-pyridinyl)-1H—imidazol-4-yl]-4-(2-thiazolyl)-1-piperazineethanol | 147(2) |
| 4-(2-chlorophenyl)-α-[5-methyl-2-(3-pyridinyl)-1H—imidazol-4-yl]-1-piperazineethanol | 148(2) |
| α-[5-methyl-2-(3-pyridinyl)-1H—imidazol-4-yl]-4-(2-pyrimidinyl)-1-piperazineethanol | 140(4) |
| 4-(3-chlorophenyl)-α-[5-methyl-2-(3-pyridinyl)-1H—imidazol-4-yl]-1-piperazine- | 132(3) |

TABLE I-continued

Hypotensive Activity in Spontaneously Hypertensive Rats

| Compound | Average MABP mm Hg (No. of Rats) |
| --- | --- |
| 4-(4-fluorophenyl)-α-[5-methyl-2-(3-methyl-4-pyridinyl)-1H—imidazol-4-yl]-1-piperazineethanol | 84(2) |
| 4-(2-methylphenyl)-α-[5-methyl-2-(3-pyridinyl)-1H—imidazol-4-yl]-1-piperazineethanol | 112(2) |
| 4-(3-methylphenyl)-α-[5-methyl-2-(3-pyridinyl)-1H—imidazol-4-yl]-1-piperazineethanol | 123(4) |
| 4-(4-fluorophenyl)-α-[5-methyl-2-(4-pyridinyl)-1H—imidazol-4-yl]-1-piperazineethanol | 100(2) |
| 4-(4-fluorophenyl)-α-[5-methyl-2-(2-pyridinyl)-1H—imidazol-4-yl]-1-piperazineethanol | 105(2) |
| 4-(4-fluorophenyl)-α-[5-methyl-2-(3-pyridinyl)-1H—imidazol-4-yl]-α-phenyl-1-piperazineethanol | 101(2) |

The novel compounds of the present invention have been found to be highly useful for lowering elevated blood pressure in mammals when administered in amounts ranging from about 0.4 mg to about 10.0 mg/kg of body weight per day. A preferred dosage regimen for optimum results would be from about 7.0 mg to about 175 mg per dose. Such dosage units are employed that a total of from about 28 mg to about 700 mg of active compound for a subject of about 70 kg of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as the intravenous route.

The compounds of the present invention may be administered as active components of compositions in unit dosage form such as tablets, pills, capsules, powders, granules, oral or parenteral solutions or suspensions and the like. For preparing solid compositions such as tablets, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

Compositions according to the present invention having the desired clarity, stability and adaptability for parenteral use are obtained by dissolving from 0.10% to 10% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite and sodium formaldehyde sulfoxylate. Generally, from about 0.05 to about 0.2% concentrations of antioxidant are employed.

The novel compounds of the present invention are adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier, or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in the specification, these being features of the present invention.

The invention will be described in greater detail in conjunction with the following specific examples.

EXAMPLE 1

1-[5-Methyl-2-(3-pyridinyl)-1H-imidazol-4-yl]ethanone

The compound 2,3,4-pentanetrione, 3-oxime was prepared from 2,4-pentanedione by the methods described in Beilstein, Vol. I, 807, 3rd Edition and by L. Wolff, Ann., 325, 139.

A mixture of 6.5 g of 2,3,4-pentanetrione, 3-oxime and 6.0 g of 3-pyridylmethylamine in 125 ml of acetonitrile was stirred at reflux temperature for 2.5 hours, then cooled at −10° C. The resulting precipitate was collected, washed with 25 ml of cold dichloromethane, air dried and then recrystallized from acetonitrile, giving 5.3 g of the desired compound as a pale yellow solid, mp 198°–199° C.

EXAMPLE 2

1-[5-Methyl-2-(3-methyl-4-pyridinyl)-1H-imidazol-4-yl]ethanone

A mixture of 7.1 g of 3-methyl-4-pyridylmethylamine, 6.25 g of 2,3,4-pentanetrione, 3-oxime and 125 ml of acetonitrile was stirred at reflux temperature for 5 hours, then cooled at −10° C. The resulting precipitate was collected, washed with cold acetonitrile, dried and then recrystallized from a mixture of chloroform and hexane, giving 4.5 g of the desired compound, mp 185°–187° C.

EXAMPLE 3

1-[5-Methyl-2-(2-pyridinyl)-1H-imidazol-4-yl]ethanone

A mixture of 6.5 g of 2,3,4-pentanetrione, 3-oxime and 6.0 g of 2-pyridylmethylamine in 125 ml of acetonitrile was reacted as described in Example 1, giving 3.6 g of the desired compound, mp 145°–147° C.

EXAMPLE 4

1-[5-Methyl-2-(4-pyridinyl)-1H-imidazol-4-yl]ethanone

A mixture of 6.5 g of 2,3,4-pentanetrione, 3-oxime and 6.0 g of 4-pyridylmethylamine in 75 ml of N,N-dimethylformamide was stirred at reflux temperature for 4 hours, then the solvent was removed in vacuo and 100 ml of acetonitrile was added to the residual oil. This mixture was boiled, then cooled at −10° C. The resulting precipitate was collected, washed with 50 ml of cold acetonitrile, air dried and then recrystallized from 150 ml of boiling acetonitrile after treatment with activated charcoal by cooling at −10° C., giving 4.0 g of the desired compound as a tan solid, mp 181°–183° C.

EXAMPLE 5

2-Bromo-1-[5-methyl-2-(3-pyridinyl)-1H-imidazol-4-yl]ethanone and the corresponding dihydrobromide salt To a stirred solution of 10 g of 1-[5-methyl-2-(3-pyridinyl)-1H-imidazol-4-yl]ethanone in 60 ml of 48% hydrobromic acid at 80° C. was added, dropwise during 5–10 minutes, 2.8 ml of bromine. After addition was complete, the mixture was stirred at 80° C. for 10 minutes, then allowed to cool to room temperature. The resulting solid was collected, washed with three 25 ml portions of acetone and dried, giving 13.4 g of 2-bromo-1-[5-methyl-2-(3-pyridinyl)-1H-imidazol-4-yl]ethanone, dihydrobromide.

An 11.7 g portion of the above dihydrobromide derivative was added to 510 ml of 0.1N sodium hydroxide, stirred for 20 minutes and the solid collected, washed with water and dried, giving 6.9 g of the base form of the desired compound as an off-white solid, mp 285°–295° C.

Following the procedure of Example 5, but using the unbrominated ethanones of Examples 2–4 and without using the final step which converts the dihydrobromide salt to the base, the compounds of Example 6–8, found in Table II, were obtained.

TABLE II

| Ex. | Starting Material of Ex. | Compound | MP °C. |
|---|---|---|---|
| 6 | 2 | 2-bromo-1-[5-methyl-2-(3-methyl-4-pyridinyl)-1H—imidazol-4-yl]-ethanone, dihydrobromide | 225–230 (dec.) |
| 7 | 3 | 2-bromo-1-[5-methyl-2-(2-pyridinyl)-1H—imidazol-4-yl]ethanone, dihydrobromide | |
| 8 | 4 | 2-bromo-1-[5-methyl-2-(4-pyridinyl)-1H—imidazol-4-yl]ethanone, dihydrobromide | |

EXAMPLE 9

1-[5-Methyl-2-(3-pyridinyl)-1H-imidazol-4-yl]-2-(4-phenyl-1-piperazinyl)ethanone To a stirred suspension of 4 g of 2-bromo-1-[5-methyyl-2-(3-pyridinyl)-1H-imidazol-4-yl]ethanone in 50 ml of dry tetrahydrofuran was added rapidly a mixture of 2.3 g of 1-phenylpiperazine and 1.4 g of triethylamine in 5 ml of dry tetrahydrofuran. This mixture was stirred for one hour and then filtered. Evaporation of the filtrate left a gummy foam which became amorphous upon trituration with 200 ml of ether. This solid was collected, washed with ether, suspended in 6 ml of acetone and stirred for 15 minutes. The solid was collected, washed repeatedly with acetone and then dried, giving 2.6 g of the desired intermediate, mp 141°–152° C. (dec.).

Following the procedure of Example 9, using the compounds of Examples 5–8 (as the base or the dihydrobromide salt) and the indicated piperazine derivatives the intermediates of Examples 10–24 found in Table III were obtained.

TABLE III

| Ex. | Product of Example (2HBr, base) | Piperazine Derivative | Intermediate | Yield g | MP °C. |
|---|---|---|---|---|---|
| 10 | 5 (base) | 4-fluorophenyl | 2-[4-(4-fluorophenyl)-1-piperazinyl]-1-[5-methyl-2-(3-pyridinyl)-1H—imidazol-4-yl]ethanone | 4.3 | 184–185 |
| 11 | 5 (base) | 3-(trifluoromethyl)phenyl | 1-[5-methyl-2-(3-pyridinyl)-1H—imidazol-4-yl]-2-[4-[3-(trifluoromethyl)phenyl]-1-piperazinyl]ethanone | 7.9 | 110–115 (dec.) |
| 12 | 5 (base) | 2-methoxyphenyl | 2-[4-(2-methoxyphenyl)-1-piperazinyl]-1-[5-methyl-2-(3-pyridinyl)-1H—imidazol-4-yl]ethanone | 3.2 | 199–203 |
| 13 | 5 (base) | 4-methoxyphenyl | 2-[4-(4-methoxyphenyl)-1-piperazinyl]-1- | 2.2 | 116–120 |

TABLE III-continued

| Ex. | Product of Example (2HBr, base) | Piperazine Derivative | Intermediate | Yield g | MP °C. |
|---|---|---|---|---|---|
| 14 | 5 (base) | 4-chlorophenyl | [5-methyl-2-(3-pyridinyl)-1H—imidazol-4-yl]ethanone 2-[4-(4-chlorophenyl)-1-piperazinyl]-1-[5-methyl-2-(3-pyridinyl)-1H—imidazol-4-yl]ethanone | 3.2 | 172–175 |
| 15 | 5 (2HBr) | 3-chlorophenyl | 2-[4-(3-chlorophenyl)-1-piperazinyl]-1-[5-methyl-2-(3-pyridinyl)-1H—imidazol-4-yl]ethanone | 3.4 | 115–120 (dec.) |
| 16 | 5 (2HBr) | 2-chloro-11-(1-piperazinyl)dibenz[b,f][1,4]oxazepine | 2-[4-(2-chlorodibenzo[b,f][1,4]oxazepin-11-yl)-1-piperazinyl]-1-[5-methyl-2-(3-pyridinyl)-1H—imidazol-4-yl]ethanone | 4.0 | 180 (dec.) |
| 17 | 5 (2HBr) | 2-thiazolyl | 1-[5-methyl-2-(3-pyridinyl)-1H—imidazol-4-yl]-2-[4-(2-(thiazolyl)-1-piperazinyl]-ethanone | 4.4 | 89–91 |
| 18 | 5 (2HBr) | 2-chlorophenyl | 2-[4-(2-chlorophenyl)-1-piperazinyl]-1-[5-methyl-2-(3-pyridinyl)-1H—imidazol-4-yl]ethanone | 3.03 | 191–195 |
| 19 | 5 (2HBr) | 4-(2-pyrimidinyl) | 1-[5-methyl-2-(3-pyridinyl)-1H—imidazol-4-yl]-2-[4-(2-(pyrimidinyl)-1-piperazinyl]ethanone | 2.7 | 169–172 (dec.) |
| 20 | 6 (2HBr) | 4-fluorophenyl | 2-[4-(4-fluorophenyl)-1-piperazinyl]-1-[5-methyl-2-(3-methyl-4-pyridinyl)-1H—imidazol-4-yl]ethanone | 1.75 | 170–172 |
| 21 | 7 (2HBr) | 4-fluorophenyl | 2-[4-(4-fluorophenyl)-1-piperazinyl]-1-[5-methyl-2-(2-pyridinyl)-1H—imidazol-4-yl]ethanone | 1.52 | 159–161 |
| 22 | 8 (2HBr) | 4-fluorophenyl | 2-[4-(4-fluorophenyl)-1-piperazinyl]-1-[5-methyl-2-(4-pyridinyl)-1H—imidazol-4-yl]ethanone | 0.75 | 230–233 |
| 23 | 5 (2HBr) | 2-methylphenyl | 2-[4-(2-methylphenyl)-1-piperazinyl]-1-[5-methyl-2-(3-pyridinyl)-1H—imidazol-4-yl]ethanone | 1.68 | 198–200 |
| 24 | 5 (2HBr) | 3-methylphenyl | 2-[4-(3-methylphenyl)-1-piperazinyl]-1-[5-methyl-2-(3-pyridinyl)-1H—imidazol-4-yl]ethanone | 5.4 | 138–140 |

EXAMPLE 25

α-[5-Methyl-2-(3-pyridinyl)-1H-imidazol-4-yl]-4-phenyl-1-piperazineethanol

To a suspension of 1 g of 1-[5-methyl-2-(3-pyridinyl)-1H-imidazol-4-yl]-2-(4-phenyl-1-piperazinyl)ethanone in 5 ml of methanol, cooled in an ice-water bath, was added 0.2 g of sodium borohydride. After gas evolution ceased, this mixture was stirred in the bath for 45 minutes, with the addition of 2 ml of methanol after 5 minutes, and then at room temperature for one hour. A 0.1 g portion of sodium borohydride was added, the mixture was stirred in the ice-water bath for 30 minutes, then at room temperature for one hour. The addition of 0.1 g of sodium borohydride and the reaction conditions were repeated twice more, then the mixture was poured into ice-water. The mixture was adjusted to pH 7–8 with glacial acetic acid. The gummy solid was collected, washed with water and then triturated with 30 ml of ether for 15 minutes. The ether was decanted and the solid triturated with 10 ml of fresh ether. The solid was collected, washed with ether and dried in vacuo, giving 0.6 g of the desired product as a pale yellow solid, mp 180°–184° C. (dec.).

Following essentially the procedure of Example 25, the products of Examples 26–40, found in Table IV, were obtained.

TABLE IV

| Ex. | Intermediate of Example | Product | Yield g | MP °C. |
|---|---|---|---|---|
| 26 | 10 | 4-(4-fluorophenyl)-α-[5-methyl-2-(3-pyridinyl)-1H—imidazol-4-yl]-1-piperazineethanol | 1.5 | 195–196 |
| 27 | 11 | α-[5-methyl-2-(3-pyridinyl)-1H—imidazol-4-yl]-4-[3-(trifluoromethyl)phenyl]-1-piperazineethanol | 2.7 | 186–187 |
| 28 | 12 | 4-(2-methoxyphenyl)-α-[5-methyl-2-(3-pyridinyl)-1H—imidazol-4-yl]-1-piperazineethanol | 2.7 | 170–173 |
| 29 | 14 | 4-(4-chlorophenyl)-α-[5-methyl-2-(3-pyridinyl)-1H—imidazol-4-yl]-1-piperazineethanol | 2.4 | 201–202 |
| 30 | 13 | 4-(4-methoxyphenyl)-α-[5-methyl-2-(3-pyridinyl)-1H—imidazol-4-yl]-1-piperazineethanol | 3.4 | 190–191 |
| 31 | 16 | 4-(2-chlorodibenzo)[b,f][1,4]oxazepin-11-yl)-α-[5-methyl-2-(3-pyridinyl)-1H—imidazol-4-yl]-1-piperazineethanol | 2.8 | |
| 32 | 17 | α-[5-methyl-2-(3-pyridinyl)-1H—imidazol-4-yl]-4-(2-thiazolyl)-1-piperazineethanol | 1.8 | 193–194 |
| 33 | 18 | 4-(2-chlorophenyl)-α-[5-methyl-2-(3-pyridinyl)-1H—imidazol-4-yl]-1-piperazineethanol | 3.1 | 201–202 |
| 34 | 19 | α-[5-methyl-2-(3-pyridinyl)-1H—imidazol-4-yl]-4-(2-pyrimidinyl)-1-piperazineethanol | 1.0 | 170–172 |
| 35 | 15 | 4-(3-chlorophenyl)-α-[5-methyl-2-(3-pyridinyl)-1H—imida- | 5.6 | 181–184 |

TABLE IV-continued

| Ex. | Intermediate of Example | Product | Yield g | MP °C. |
|---|---|---|---|---|
| | | zol-4-yl]-1-piperazineethanol | | |
| 36 | 20 | 4-(4-fluorophenyl)-α-[5-methyl-2-(3-methyl-4-pyridinyl)-1H—imidazol-4-yl]-1-piperazineethanol | 1.1 | 132–135 |
| 37 | 23 | 4-(2-methylphenyl)-α-[5-methyl-2-(3-pyridinyl)-1H—imidazol-4-yl]-1-piperazineethanol | 1.6 | 211–212 |
| 38 | 24 | 4-(3-methylphenyl)-α-[5-methyl-2-(3-pyridinyl)-1H—imidazol-4-yl]-1-piperazineethanol | 2.9 | 187–188 |
| 39 | 21 | 4-(4-fluorophenyl)-α-[5-methyl-2-(2-pyridinyl)-1H—imidazol-4-yl]-1-piperazineethanol | 0.9 | 164–165 |
| 40 | 22 | 4-(4-fluorophenyl)α-[5-methyl-2-(4-pyridinyl)-1H—imidazol-4-yl]-1-piperazineethanol | 3.3 | 209–210 |

EXAMPLE 41

4-(4-Fluorophenyl)-α-methyl-α-[5-methyl-2-(3-pyridinyl)-1H-imidiazol-4-yl]-1-piperazineethanol To a stirred suspension of 1.5 g of 2-[4-(4-fluorophenyl)-1-piperazinyl]-1-[5-methyl-2-(3-pyridinyl)-1H-imidazol-4-yl]ethanone in 20 ml of dry tetrahydrofuran, cooled in an ice-water bath, was added dropwise 6 ml of 3.1M methyl magnesium bromide in ether during 5 minutes producing an exotherm. This mixture was stirred in the ice-water bath for 30 minutes, then at room temperature for 2 hours, and then poured into ice-water and adjusted to pH 7 with glacial acetic acid. The resulting yellow oil was extracted with ethyl acetate, dried and evaporated giving 1.5 g of off-white amorphous solid. This solid was dissolved in 3 ml of methanol, 25 ml of ether was added and the mixture was allowed to evaporate. The resulting orange gum was triturated with 50 ml of petroleum ether for 6 hours. The resulting solid was collected, washed with petroleum ether and dried in vacuo, giving 1.2 g of the desired product as a pale orange solid, mp 156°–162° C.

EXAMPLE 42

4-(4-Fluorophenyl)-α-[5-methyl-2-(3-pyridinyl)-1H-imidazol-4-yl]-α-phenyl-1-piperazineethanol A mixture of 1.5 g of 2-[4-(4-fluorophenyl)-1-piperazinyl]-1-[5-methyl-2-(3-pyridinyl)-1H-imidazol-4-yl]ethanone in 20 ml of dry tetrahydrofuran and 10 ml of 1.7M phenyl magnesium bromide in 10 ml of ether was reacted as described in Example 41 giving 2 g of a foam. This foam was purified by chromatography, giving 0.75 g of the desired product as a light yellow foam.

EXAMPLE 43

4-(4-Fluorophenyl)-α-[5-methyl-2-(3-pyridinyl)-1H-imidazol-4-yl]-1-piperazineethanol, tartarate A 1.91 g portion of 4-(4-fluorophenyl)-α-[5-methyl-2-(3-pyridinyl)-1H-imidazol-4-yl]-1-piperazineethanol ethanol was dissolved in 75 ml of warm ethanol. A solution of 0.75 g of dl-tartaric acid in 10 ml of ethanol was added, the mixture was warmed until solution was complete and then allowed to stand at room temperature. The resulting solid was collected, washed with ether and dried, giving 1.8 g of the desired tartarate salt, mp 80° C. (dec.).

We claim:

1. A compound selected from the group consisting of those of the formula:

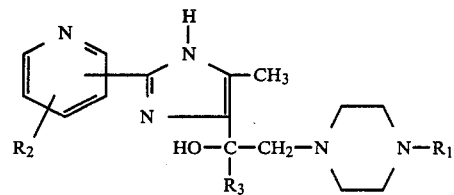

wherein $R_1$ is phenyl, monosubtituted phenyl [wherein the substituents are fluoro, chloro, bromo, trifluoromethyl, alkyl ($C_1$-$C_3$) or alkoxy ($C_1$-$C_3$)], 2-thiazxolyl, 2-pyrimidinyl or 2-chlorodibenzo [b,f][1,4]oxazepin-11-yl, $R_2$ is hydrogen or alkyl ($C_1$-$C_3$) and $R_3$ is hydrogen, phenyl or alkyl ($C_1$-$C_3$); and the pharmacologically acceptable acid-addition salts thereof.

2. The compound according to claim 1; 4-phenyl-α-[5-methyl-2-(3-pyridinyl)-1H-imidazol-4-yl]-1-piperazineethanol.

3. The compound according to claim 1; 4-(4-fluorophenyl)-α-[5-methyl-2-(3-pyridinyl)-1H-imidazol-4-yl]-1-piperazineethanol.

4. The compound according to claim 1; 4-(3-trifluoromethylphenyl-α-[5-methyl-2-(3-pyridinyl)-1H-imidazol-4-yl]-1-piperazineethanol.

5. The compound according to claim 1; 4-(2-methoxyphneyl)-α-[5-methyl-2-(3-pyridinyl)-1H-imidazol-4-yl]-1-piperazineethanol.

6. The compound according to claim 1; 4-(4-chlorophenyl)-α-[5-methyl-2-(3-pyridinyl)-1H-imidazol-4-yl]-1-piperazineethanol.

7. The compound according to claim 1; 4-(4-methoxyphenyl)-α-[5-methyl-2-(3-pyridinyl)-1H-imidazol-4-yl]-1-piperazineethanol.

8. The compound according to claim 1; 4-(2-chlorodibenzo[b,f][1,4]oxazepin-11-yl)-α-[5-methyl-2-(3-pyridinyl)-1H-imidazol-4-yl]-1-piperazineethanol.

9. The compound according to claim 1; 4-(2-thiazolyl)-α-[5-methyl-2-(3-pyridinyl)-1H-imidazol-4-yl]-1-piperazineethanol.

10. The compound according to claim 1; 4-(2-chlorophenyl)-α-[5-methyl-2-(3-pyridinyl)-1H-imidazol-4-yl]-1-piperazineethanol.

11. The compound according to claim 1; 4-(2-pyrimidinyl)-α-[5-methyl-2-(3-pyridinyl)-1H-imidazol-4-yl]-1-piperazineethanol.

12. The compound according to claim 1; 4-(3-chlorophenyl)-α-[5-methyl-2-(3-pyridinyl)-1H-imidazol-4-yl]-1-piperazineethanol.

13. The compound according to claim 1; 4-(4-fluorophenyl)-α-[5-methyl-2-(3-methyl-4-pyridinyl)-1H-imidazol-4-yl]-1-piperazineethanol.

14. The compound according to claim 1; 4-(2-methylphenyl)-α-[5-methyl-2-(3-pyridinyl)-1H-imidazol-4-yl]-1-piperazineethanol.

15. The compound according to claim 1; 4-(3-methylphenyl)-α-[5-methyl-2-(3-pyridinyl)-1H-imidazol-4-yl]-1-piperazineethanol.

16. The compound according to claim 1; 4-(4-fluorophenyl)-α-[5-methyl-2-(2-pyridinyl)-1H-imidazol-4-yl]-1-piperazineethanol.

17. The compound according to claim 1: 4-(4-fluorophenyl)-α-[5-methyl-2-(4-pyridinyl)-1H-imidazol-4-yl]-1-piperazineethanol.

18. The compound according to claim 1; 4-(4-fluorophenyl)-α-methyl-α-[5-methyl-2-(3-pyridinyl)-1H-imidazol-4-yl]-1-piperazineethanol.

19. The compound according to claim 1; 4-(4-fluorophenyl)-α-[5-methyl-2-(3-pyridinyl)-1H-imidazol-4-yl]-α-phenyl-1-piperazineethanol.

20. The compound according to claim 1; 4-(4-fluorophenyl)-α-[5-methyl-2-(3-pyridinyl)-1H-imidazol-4-yl]-1-piperazineethanol, tartrate.

21. A method of treating hypertension in a warm-blooded animal which comprises administering to said animal a hypotensive amount of a compound of claim 1.

22. A hypotensive composition of matter dosage unit form comprising from 50 to 1000 mg of a compound of claim 1 in association with a pharmaceutically acceptable carrier.

23. A compound of the formula:

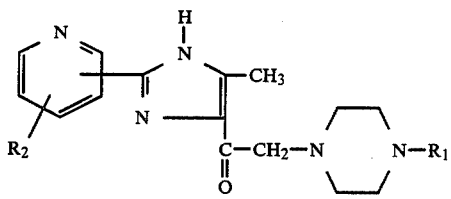

wherein $R_1$ is phenyl, monosubstituted phenyl [wherein the substituents are fluoro, chloro, bromo, trifluoromethyl, alkyl ($C_1$–$C_3$) or alkoxy ($C_1$–$C_3$)],2-thiazolyl, 2-pyrimidinyl or 2-chlorodibenzo [b,f][1,4] oxazepin-11-yl and $R_2$ is hydrogen or alkyl ($C_1$–$C_3$).

* * * * *